US010792447B2

(12) United States Patent
Walsh et al.

(10) Patent No.: US 10,792,447 B2
(45) Date of Patent: Oct. 6, 2020

(54) BREATH ACTUATED INHALER

(71) Applicant: Norton (Waterford) Limited, Waterford (IE)

(72) Inventors: Declan Walsh, Waterford (IE); Paul Prendergast, Waterford (IE); Daniel Buck, Waterford (IE); Trevor Kent, Waterford (IE); Niall Thompson, Waterford (IE)

(73) Assignee: NORTON (WATERFORD) LIMITED, Waterford (IE)

( * ) Notice: Subject to any disclaimer, the term of this patent is extended or adjusted under 35 U.S.C. 154(b) by 0 days.

(21) Appl. No.: 16/258,330

(22) Filed: Jan. 25, 2019

(65) Prior Publication Data

US 2019/0262602 A1    Aug. 29, 2019

(30) Foreign Application Priority Data

Jan. 26, 2018  (GB) .................................. 1801309.4

(51) Int. Cl.
*A61M 39/24* (2006.01)
*A61M 15/00* (2006.01)
(Continued)

(52) U.S. Cl.
CPC ......... *A61M 15/0095* (2014.02); *A61K 31/46* (2013.01); *A61K 31/575* (2013.01);
(Continued)

(58) Field of Classification Search
CPC .......... A61M 15/0091; A61M 15/0093; A61M 15/0095; A61M 15/0096; A61M 15/009;
(Continued)

(56) References Cited

U.S. PATENT DOCUMENTS

2007/0056580 A1* 3/2007 Jones .................. A61M 15/009
128/200.23
2007/0056585 A1* 3/2007 Davies .............. A61M 15/0065
128/203.15
(Continued)

FOREIGN PATENT DOCUMENTS

| GB | 2263873 | 11/1993 |
|---|---|---|
| JP | 5207855 B2 | 6/2013 |
| WO | 0193933 A2 | 12/2001 |

OTHER PUBLICATIONS

European Search Opinion for EP 19 15 3824 dated Sep. 12, 2019; 6 pages.
(Continued)

*Primary Examiner* — Colin W Stuart
*Assistant Examiner* — Douglas Y Sul
(74) *Attorney, Agent, or Firm* — Morgan, Lewis & Bockius LLP

(57) ABSTRACT

A breath actuated metered dose inhaler may include a canister fire system configured to fire a medicament containing canister in response to patient inhalation. The canister fire system may include a pneumatic force holding unit and having a rest configuration in which a metering valve of the canister is in a refill configuration; a prepared configuration in which a canister actuation force is retained by the pneumatic force holding unit and the canister fire system is actuatable by patient inhalation induced airflow; and a fire configuration in which the metering valve is in a dose delivery position. When in the prepared configuration, the force retained by the so pneumatic force holding unit may be reduced by less than about 6% over a period of 5 minutes, preferably less than about 3% over a period of 5 minutes.

10 Claims, 9 Drawing Sheets

(51) Int. Cl.
*A61M 16/20* (2006.01)
*A61M 16/00* (2006.01)
*A61K 31/46* (2006.01)
*A61K 31/575* (2006.01)
*B29C 45/37* (2006.01)

(52) U.S. Cl.
CPC ........ *A61M 15/009* (2013.01); *A61M 16/208* (2013.01); *A61M 39/24* (2013.01); *A61M 15/0026* (2014.02); *A61M 15/0068* (2014.02); *A61M 2016/0015* (2013.01); *A61M 2039/242* (2013.01); *A61M 2039/244* (2013.01); *A61M 2202/064* (2013.01); *A61M 2207/10* (2013.01); *B29C 45/37* (2013.01); *B29K 2995/0072* (2013.01); *B29K 2995/0073* (2013.01)

(58) Field of Classification Search
CPC ............... A61M 11/08; A61M 16/208; A61M 15/0026; A61M 2207/00; A61M 2207/10; A61M 2016/0015; A61M 2039/242; A61M 2039/244
See application file for complete search history.

(56) References Cited

U.S. PATENT DOCUMENTS

| | | | |
|---|---|---|---|
| 2008/0314383 A1* | 12/2008 | Barney | A61M 15/0065 128/203.15 |
| 2010/0012115 A1* | 1/2010 | Bacon | A61M 15/0065 128/200.23 |
| 2010/0065050 A1* | 3/2010 | Holroyd | A61M 15/0091 128/203.15 |
| 2016/0325057 A1* | 11/2016 | Morrison | A61M 15/0071 |

OTHER PUBLICATIONS

European Search Report for EP 19 15 3824 dated Sep. 12, 2019; 4 pages.
European Partial Search Report for EP 19 15 3824 dated May 2, 2019; 4 pages.
European Provisional Opinion for EP 19 15 3824 dated May 2, 2019; 4 pages.

* cited by examiner

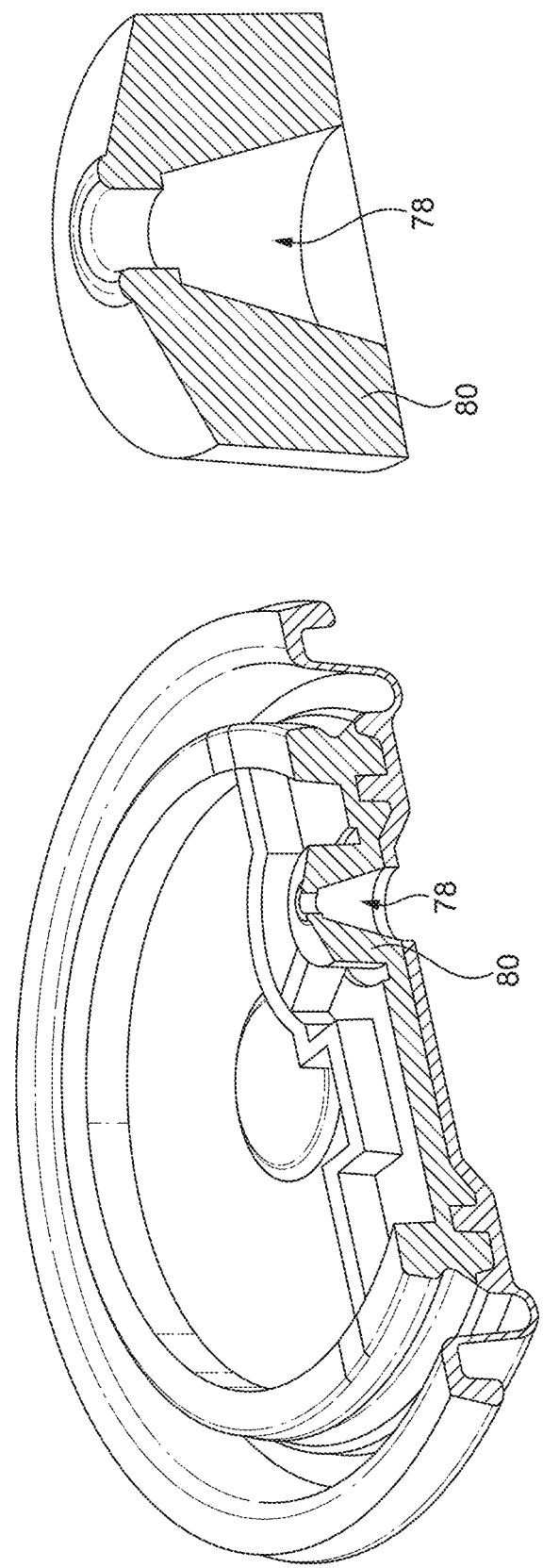

BREATH ACTUATED INHALER

CROSS-REFERENCE TO RELATED APPLICATION

This application claims the benefit of priority of Great Britain Patent Application No. 1801309.4 filed on Jan. 26, 2018, the entire disclosure of which is incorporated herein by reference in its entirety for all purposes.

FIELD OF THE INVENTION

The present invention relates to a metered dose inhaler and, in particular, a breath actuated metered dose inhaler. The invention further provides valve port and a diaphragm for a pneumatic force holding unit of a breath actuated metered dose inhaler, a flap valve for the canister fire system of a breath actuated metered dose inhaler, as well as methods for manufacturing and assembling the same.

BACKGROUND TO IN THE INVENTION

Inhalers for delivering medicament to a patient by inhalation are known. Such devices include metered dose inhalers (of both pressurised and dry-powder types). Metered dose inhalers typically comprise a medicament-containing vessel and an actuator housing having a medicament delivery outlet in the form of a mouthpiece or nosepiece.

The medicament-containing vessel may be a pressurized canister containing a mixture of active medicament and propellant. Such canisters are usually formed from a deep-drawn aluminium cup having a crimped lid which carries a metering valve assembly. The metering valve assembly is provided with a protruding valve stem which, in use, is inserted as a tight push fit into a stem block in the actuator housing.

Metered-dose inhalers may either be of the manually operable type or the breath actuated type. For the manually operable type, the patient self-administers the medicament by manually pressing the closed end of the canister into the actuator housing to cause movement of the canister relative to its valve stem (which is fixed in the stem block of the actuator housing). This movement is sufficient to actuate the metering valve assembly of the canister, resulting in the pressurised contents of a metering chamber being vented through the stem, through the stem block and its exit orifice, and causing the medicament to exit the mouthpiece or nosepiece as an aerosol mist. Simultaneously with this action, the patient inhales through the nosepiece or mouthpiece, entraining the aerosol mist in the inhaled stream of air. The patient then releases the depression force on the canister which, under the action of an internal valve spring, moves upward with respect to the valve stem, returning to its resting position.

A more recent development is the so-called breath actuated metered-dose inhaler, which serves to automatically displace the canister relative to its valve stem and release the contents of the canister's metering chamber in response to a patient's inhalation. The general purpose of such inhalers is to alleviate difficulties in coordinating actuation of the metering valve assembly with the patient's inhalation, and to provide for a maximal amount of medication to be drawn into the patient's lungs.

A known breath actuated inhaler, disclosed in WO9209323A1 and WO0193933A2, which are incorporated herein by reference, has a pressurised canister and a metering valve for controlling the ejection of inhalable substances from the canister. The canister is operable by a force holding unit having a cap housing attachable to a main housing of the inhaler. In use, a mouthpiece cap is opened to prepare the inhaler ready for inhalation and then after inhalation the mouthpiece cap is closed to reset the force holding unit, i.e. return it to a rest configuration. The force holding unit holds the force for actuating the canister until it is required.

The force holding unit comprises a compression spring, a lower cap that engages the canister, a diaphragm attached to an upper surface of the lower cap, and a pivotally mounted flap valve for selectively sealing a valve port located in the diaphragm.

In use, when the mouthpiece cap is opened, the lower cap is forced downwards under the action of the compression spring. Then, as the lower cap moves down, an enclosed volume between the diaphragm and the lower cap is increased by a linear amount, and whilst valve port remains closed, this creates a pressure difference in the enclosed volume.

The offset of the differential between the pressure in the enclosed volume and atmospheric pressure results in the lower cap resisting action of the compression spring. Downward movement of the lower cap continues until the force is balanced between the force of the compression spring and the opposing forces of the pressure difference and metering valve. This is a prepared configuration.

The geometry of the mechanism is arranged such that the balance occurs before the valve has been actuated.

Flow of air across a vane on the flap valve during inhalation causes the valve to pivot, moving the flap valve seal out of its rest position, and opening a valve channel in the diaphragm. The subsequent passage of air into the volume between the diaphragm and the lower cap allows the volume to reach atmospheric pressure. The resulting imbalance of forces acting on the lower cap and canister produces the downward motion of the canister and actuation of the aerosol metering valve: releasing a measured dose through the dispensing nozzle and into the mouthpiece.

Referring to FIGS. 1 and 2 a known diaphragm assembly 640 for use with a breath actuated inhaler is shown.

The moulded flexible diaphragm 640 includes a rigid disc-like section 641, a flexible generally cylindrical wall section, or annular flexure 645, and a thicker connector section, or peripheral attachment ring 647. A central portion is unitarily formed with and extends radially inwardly from the annular flexure 645. The central portion is provided in the form of a disk bonded along a top surface to a bottom surface of the rigid disc-like section 641, i. e., surfaces substantially transverse to the central axis of the diaphragm 640.

The relatively thick disk-portion is moulded from a rigid material (relatively high stiffness) such as acrylonitrile butadiene styrene (ABS), which is particularly resistant to flexural deformation.

The relatively thin flexure portion which includes the central portion, the annular flexure 645 and the peripheral attachment ring 647, is moulded from an optimally flexible material (relatively low stiffness) such as a thermoplastic elastomer (TPE), permitting high performance. The multi-material diaphragm 640 may be manufactured using a multi-shot moulding process.

As shown in FIGS. 1 and 2, the central portion and the rigid disc-like section 641 both define a central upwardly extending boss 702 for additional strength. In addition, the rigid disc-like section 641 includes an outer axial wall 704 which provides further strength to the diaphragm 640. The central portion includes axial walls which are received within and bonded to axial grooves of the rigid disc-like section 641, thereby providing bonding surfaces substantially parallel with the central axis of the diaphragm 640 and increasing the total bonding surface area between the central portion and the rigid disc-like section 641.

In use, the peripheral attachment ring 647 of the diaphragm 640 is fitted around an annular wall of the lower cap and is secured in an air-tight manner thereon with a retainer ring by snap-fitting. The retainer ring also provides a snug fit for one end of the compression spring, such that the compression spring is thus located and free to act on the sleeve.

The valve channel 690 of the diaphragm 640 passes through the rigid disc-like section 641 and the central portion of the diaphragm. The valve channel 690 is closed by a valve seal (not shown), which is biased closed by a flat spring. The rigid disc-like section 641 of the diaphragm includes protrusions 712 extending upwardly therefrom that receive and correctly position a flat spring. The rigid disc-like section 641 of the diaphragm 640 also includes a baffle 714 on a top surface thereof for substantially preventing air flow between the valve seal and the diaphragm.

The rigid disc-like section 641 of the diaphragm 640 additionally includes an assembly location key 716 for use in correctly assembling the diaphragm 640 within the actuator assembly.

As better illustrated in FIG. 3, a valve port 301 comprising an annular boss 302 defines the valve orifice channel 690. The boss 302 comprises two radially outwardly extending projections 303, 304 each defining a path through which polymer passed to form the boss 302 during injection moulding. The boss 302 comprises a circumferential side wall 307, a radially extending upper surface 308, including a sealing surface 309. The radially outwardly extending projections 303, 304 are circumferentially offset, and their upper surfaces 305, 306 intersect the vertical side wall 307 of the boss 302.

When using inhalers similar to those discussed above, it was observed that on occasion patients may not receive a measured dose upon inhalation, i.e. the canister does not fire.

Following these observations, an investigation by the inventors found that the missed dose of medicament may be because of unintentional actuation of the inhaler. The investigation found that the unintentional actuation may occur because of unintentional misuse leading to accidental actuation, said misuse including failing to use the inhaler immediately after priming.

More specifically, the inventors found that when in the prepared position the pressure difference maintained by the force holding degraded over a relatively short period of time, allowing the lower cap to progress in a canister fire direction under the action of the compression spring. This progression may continue until the canister fires.

Once the canister has fired accidentally as a result of the degradation of the pressure difference maintained by the force holding unit, the inhaler will not fire upon subsequent inhalation and the patient will not receive the intended dose of medicament.

The present invention aims to alleviate at least to a certain extent at least one of the problems of the prior art.

SUMMARY OF THE INVENTION

Accordingly, in a first aspect the invention provides an injection moulded polymer valve port for a pneumatic force holding unit in a breath actuated metered dose inhaler. The valve port comprises an annular boss defining a valve orifice channel. The valve port further comprises two, three, four or more, radially outwardly extending projections defining a path through which polymer passed to form the boss during moulding. The radially outwardly extending projections are substantially uniformly circumferentially separated. Typically extending from a circumferential outer wall of the annular boss. Preferably, their circumferential uniformity is offset by less than about 5 degrees, preferably by less than about 2 degrees. Typically, the boss has a longitudinal axis which passes through the valve orifice port, and two radially extending projections and the valve orifice port may lie in a common plane coincident with the longitudinal axis. In a preferred arrangement, the boss comprises two circumferentially uniformly separated radially outwardly extending projections, i.e. with a central angle of 180 degrees+/−5 degrees.

It has been found that by providing a boss with radially outwardly extending projections as described, the surface finish of the valve port, in particular, immediately adjacent the valve orifice is significantly improved, allowing a better seal to be formed with a valve port seal during use. The improved seal significantly reduces the rate of degradation of the pressure difference within a pneumatic force holding unit in a prepared configuration, reducing the likelihood of accidental actuation and the breath actuated inhaler not delivering medicament upon inhalation: improving patient compliance and treatment outcomes.

In a further aspect the invention provides an injection moulded polymer valve port for a pneumatic force holding unit in a breath actuated metered dose inhaler. The valve port comprises an annular boss defining a valve orifice channel. The valve port comprises one, two, or more radially outwardly extending projections defining a path through which polymer passed to form the boss during moulding, wherein an upper surface of the one or more radially outwardly extending projections and an upper surface of the annular boss are contiguous. Preferably, the upper surface of the annular boss and the upper surface of the projection are at an angle between about 90 degrees and about 180 degrees, preferably an obtuse angle, more preferably between 120 degrees and 180 degrees.

Advantageously, it has been found that because the upper surfaces are contiguous during moulding molten polymer flows along a mould path defining the projections and does no stall as it enters the chamber defining the boss. By way of comparison, during moulding of the boss illustrated in FIG. 3, the molten polymer must travel vertically along an outer side surface of the boss from the upper surface of the projections to the boss' upper surface, stalling radial flow. Valve ports of the inventive arrangement have been found to have a surface finish that is significantly improved, in particular immediately adjacent the valve orifice. This facilitates a better sealing with a valve port seal during use. The improved seal significantly reduces the rate of degradation of the pressure difference within a pneumatic force holding unit in breath actuated inhaler in a prepared configuration, reducing the likelihood of accidental actuation and the breath actuated inhaler not delivering medicament upon inhalation: improving patient compliance and treatment outcomes.

In a further aspect the invention provides an injection moulded polymer valve port for a pneumatic force holding unit in a breath actuated metered dose inhaler, said valve port being located on a planar body and comprising an annular boss defining a valve orifice channel. The valve port further comprises one or more radially outwardly extending projections defining a path through which polymer passed to form the boss during moulding. A portion of the planar body immediately adjacent the boss has a depth that is less than or equal to a minimum thickness of the radially outwardly extending projection. Typically, the ratio of the depth of the portion immediately adjacent to the boss to the minimum thickness of the radially outwardly extending projection is from about 1:1 to about 1:2, preferably from about 1:1 to about 3:4. Typically, the portion of the planar body immediately adjacent the boss circumferentially encloses, preferably fully encloses, the boss between the one or more radially extending projections.

Typically, the portion of the planar body immediately adjacent the boss has a depth of from about 0.50 mm to about 0.70 mm, preferably from about 0.55 mm to about 0.65 mm. 0.60 mm is an example. The planar body is typically the relatively rigid disk-like portion of the diaphragm.

Additionally, or alternatively, the radially outwardly extending projections may have a thickness of from about 0.54 mm to about 0.83 mm, preferably from about 0.64 mm to about 0.73 mm. 0.68 mm is an example. Where there are two or more radially outwardly extending projections, typically they each have substantially the same thickness. The radially outwardly extending projections are typically drafted to aid mould release. In this instance the thickness relates to the minimum thickness of the projection.

Advantageously, it has been found that a boss that is surrounded by a narrowing (e.g. a narrowed portion of the planar body) concentrates polymer flow towards the upper surface of the boss during moulding. This has the effect of improving the surface finish of the valve port immediately adjacent the valve orifice, allowing a better seal to be formed with a valve port seal during use. The improved seal significantly reduces the rate of degradation of the pressure difference within a pneumatic force holding unit in a breath actuated inhaler in a prepared configuration, reducing the likelihood of accidental actuation and the breath actuated inhaler not delivering medicament upon inhalation: improving patient compliance and treatment outcomes.

In a further aspect the invention provides, a valve port for a pneumatic force holding unit in a breath actuated metered dose inhaler, said valve port comprising an annular boss with an inner wall defining a valve orifice channel wherein the volume of the orifice channel defined by the inner wall of the boss is greater than about 12.7° to of the volume of the boss, preferably from about 12.7% to about 20%, more preferably from about 13% to about 17%, 15.5% being an example, and/or wherein the inner wall defines a frustum of an imaginary cone with an apex angle of greater than about 20 degrees, preferably from about 22 degrees to about 35 degrees, more preferably from about 24 degrees to about 30 degrees. 28 degrees being an example.

Typically, the valve orifice channel has a cross-sectional area at its uppermost (i.e. sealing) end of from about 0.22 mm$^2$ to about 0.31 mm$^2$, 0.26 mm$^2$ being an example. Typically, the valve orifice channel has a substantially circular cross-section, typically along its entire length. Preferably, a portion of the wall of the valve orifice channel defines the frustum of an imaginary cone.

It has been found that by providing a boss with a high valve orifice channel volume to boss volume ratio, during injection moulding, polymer flow is concentrated towards the upper surface of the boss. Likewise, when the inner surface of the valve orifice defines the frustum of an imaginary cone with an apex of greater than 20 degrees. This has the effect of improving the surface finish of the valve port immediately adjacent the valve orifice channel opening, allowing a better seal to be formed with a valve port seal during use. As in other aspects, the improved seal significantly reduces the rate of degradation of the pressure difference within a pneumatic force holding unit of an inhaler in a prepared configuration, reducing the likelihood of accidental actuation and the breath actuated inhaler not delivering medicament upon inhalation: improving patient compliance and treatment outcomes.

In a further aspect the invention provides a valve port for a pneumatic force holding unit in a breath actuated metered dose inhaler, said valve port comprising a valve seal surface, which in use is engaged by a movable valve seal in a sealing arrangement, characterised in that the valve seal surface has a surface roughness average (RA) of 0.15 μm or less, preferably less than 0.12 μm, preferably from about 0.10 μm to about 0.01 μm.

Typically, the valve seal comprises an elastomer, preferably a thermoplastic elastomer. Preferably the thermoplastic elastomer is selected from the group consisting of styrenic block copolymers, thermoplastic olefins, thermoplastic polyurethanes, thermoplastic copolyester, thermoplastic polyimide. Advantageously thermoplastic elastomers can be injection moulded. Thermoplastic polyurethanes are particularly preferred.

The elastomer may have a hardness of from about 80 to 90 Shore A. Preferably this elastomer has a hardness of from about 82 to 87 Shore A (e.g. BASF Elastollan® 1185 A). Still more preferably, the elastomer has a hardness of about 85 Shore A.

In embodiments, the elastomer may comprise a blend of thermoplastic polyurethane elastomer and at least one release agent, typically in an amount of from about 2% to about 6% by weight, for example, Elastollan Konz. 950/1 4% from BASF.

Preferably the valve seal, when in a sealing arrangement, engages the valve seal surface with a moment of at least about 0.015 Nmm, preferably from about 0.017 Nmm to about 0.025 Nmm when in a rest configuration (e.g. with no vacuum), and from about 0.05 Nmm to about 0.11 Nmm when in a prepared configuration (e.g. with a vacuum).

The valve port may be manufacture using injection moulding; however, it will be appreciated that other methods may also be employed, e.g. spin casting, or an additive manufacturing technique: e.g. 3D printing.

By reducing the surface roughness of the valve port immediately adjacent the valve orifice an improved seal is formed with a valve port seal during use. As in other aspects, an improved seal significantly reduces the rate of degradation of the pressure difference within a pneumatic force holding unit in a prepared configuration, reducing the likelihood of accidental actuation and the breath actuated inhaler not delivering medicament upon inhalation: improving patient compliance and treatment outcomes.

In an aspect the invention provides a flap valve for the canister fire system of a breath actuated metered dose inhaler, wherein the flap valve comprises a chassis for pivotal mounting within the inhaler, a valve port according to any preceding claim, and a valve port seal mounted on the chassis configured to selectively engage the valve port in a sealing relation, and a vane for moving the valve port seal in direction away from the valve port in response to inhalation induced airflow.

In a further aspect the invention provides a diaphragm for a pneumatic force holding unit in a canister firing mechanism of a breath actuated metered dose inhaler comprising a valve port according to any previous aspect of the invention, or the flap valve according to the immediately preceding aspect. Typically, the diaphragm comprises a relatively rigid disk-like portion and relatively flexible membrane portion, and wherein the valve port is unitarily formed with the rigid disk-like portion.

The relatively rigid disk-like portion, including the valve port, is typically made from a rigid material (relatively high stiffness) such as acrylonitrile butadiene styrene, which is particularly resistant to flexural deformation. The relatively flexible portion which may include a central portion, an annular flexure and a peripheral attachment ring may be moulded from an optimally flexible material (relatively low stiffness) such as a thermoplastic elastomer. A thermoplastic polyurethane is particularly preferred.

The elastomer may have a hardness of from about 80 to 90 Shore A to about 35 to 40 Shore D. Preferably this elastomer has a hardness of from about 89 to about 90 Shore A and from about 37 to about 40 Shore D (e.g., BASF Elastollan® 1185 A). Still more preferably, the elastomer has a hardness of about 89 Shore A and about 37 Shore D.

Additionally, the elastomer comprises a blend of thermoplastic polyurethane elastomer and at least one release agent, typically in an amount of from about 2% to about 6% by weight, for example, Elastollan Konz. 950/1 4% from BASF.

In a further aspect the invention provides a mould for injection moulding a diaphragm for a breath actuated metered dose inhaler wherein the mould comprises cavities configured to produce a valve port, and/or diaphragm, according any earlier aspect of the invention. Preferably, the mould is metallic, typically steel, and has a surface average roughness (RA) of less than or equal to about 0.1 µm, preferably from about 0.025 µm to about 0.1 µm, preferably at least in the area corresponding to the sealing surface of the valve port. Typically, a SPI A3 finish is used the region of the sealing surface and a VDI-21 finish is used for the remainder of the diaphragm.

The invention further provides a method for manufacturing a diaphragm for a metered dose inhaler comprising the steps of providing a mould according to the immediately previous aspect and injecting molten polymer, or prepolymer, into the mould under pressure to form a diaphragm according to any preceding aspect of the invention.

Preferably the moulding is a two-shot moulding process. A first shot providing a relatively rigid disk like portion. A second shot providing a relatively flexible portion.

In the first shot; typically, molten polymer, e.g. ABS, is provided at a temperature of from about 220° C. to about 260° C., more preferably from about 240° C. to about 250° C., about 245° C. being an example. Typically, the polymer is injected, packed, and held at a pressure of from about 560 bar to about 840 bar, 700 bar being an example. Typically, the mould temperature is from about 30° C. to about 70° C., preferably from about 38° C. to about 48° C.: 43° C. being an example.

In the second shot, typically, molten polymer, e.g. TPE, is provided at a temperature of from about 205° C. to about 220° C., more preferably from about 205° C. to about 215° C., about 210° C. being an example. Typically, the polymer is injected, packed, and held at a pressure of from about 560 bar to about 840 bar, 700 bar being an example. Typically, the mould temperature is from about 15° C. to about 70° C.

For both the first shot and second shot, the hold time and pack time may be approximately 0.5 seconds each.

The injection time for the second shot is typically from about 0.10 seconds to about 0.15 seconds: 0.12 seconds being an example.

The injection time for the first shot is preferably greater than about 0.5 seconds, more preferably from about 1 second to about 1.5 seconds: 1.26 second being an example. Whilst short injection times of from about 0.1 second to about 0.5 seconds may be employed, it has been found that a relatively long injection time for the first shot improves the surface finish of the diaphragm, in particular weld lines, on the upper surface of the boss, particularly at the sealing surface. During injection moulding of the valve port, the polymer passes through the mould cavity portions dimensioned to form the radially outwardly extending projection(s) into the mould cavity portion dimensioned to form the boss.

The invention further provides a breath actuated metered dose inhaler comprising a valve port, flap valve, and/or diaphragm according to or manufactured according to other aspects of the invention.

In a further aspect the invention provides a breath actuated metered dose inhaler comprising a canister fire system configured to fire a canister in response to patient inhalation, the canister fire system comprising a pneumatic force holding unit and having: a rest configuration in which a metering valve of the canister is in a refill configuration; a prepared configuration in which the canister fire system is actuatable by patient inhalation induced airflow; and a fire configuration in which the metering valve is in a dose delivery position. The pneumatic force holding unit is configured such that once the inhaler is moved from the rest configuration to the prepared configuration, in the absence of an external trigger, for instance patient inhalation induced airflow, the canister fire system remains in a prepared configuration for at least about 5 minutes, preferably at least about 15 minutes, more preferably at least about 30 minutes.

Typically, once the inhaler is moved from the rest configuration to the prepared configuration in 95% of instances the canister fire system will remain in a prepared configuration for at least about 15 minutes. Preferably; once the inhaler is moved from the rest configuration to the prepared configuration in 90% of instances the canister fire system will remain in a prepared configuration for at least about 30 minutes.

Advantageously, the significantly increased time to actuation reduces the likelihood of accidental actuation and the breath actuated inhaler not delivering medicament upon inhalation: improving patient compliance and treatment outcomes.

In a further aspect, the present invention provides a breath actuated metered dose inhaler comprising a canister fire system configured to fire a canister in response to patient inhalation, the canister fire system comprising a pneumatic force holding unit and having: a rest configuration in which a metering valve of the canister is in a refill configuration; a prepared configuration in which a canister actuation force is retained by the pneumatic force holding unit and the canister fire system is actuatable by patient inhalation induced airflow; and a fire configuration in which the metering valve is in a dose delivery position; wherein when in the prepared configuration the force retained by the pneumatic force holding unit degrades by less than about 6% over a period of 5 minutes, preferably less than about 3%, preferably from about 2.7% to about 0.08%: 1.5% being an example.

Advantageously, the significantly reduced rate of degradation of the pressure difference within a pneumatic force holding unit in a prepared configuration, reduces the likelihood of accidental actuation and, therefore, the breath actuated inhaler not delivering medicament upon inhalation; improving patient compliance and treatment outcomes.

It will be appreciated that all of the aspects and embodiments herein described may be combined mutatis mutandis. Specifically; each of the valve ports disclosed may have a sealing surface with a surface roughness average (RA) of less than of less than 0.15 μm, preferably less than about 0.1 μm.

BRIEF DESCRIPTION OF THE FIGURES

Preferred features of the present invention will now be described, by way of example; with reference to the accompanying drawings; in which:

FIG. 14 shows the volume of the boss and the valve orifice channel.

DETAILED DESCRIPTION OF THE INVENTION

The invention provides a valve port for a pneumatic force holding unit in a breath actuated metered dose inhaler, breath actuated metered dose inhalers; and methods of manufacturing and assembling the same.

Figure 8:
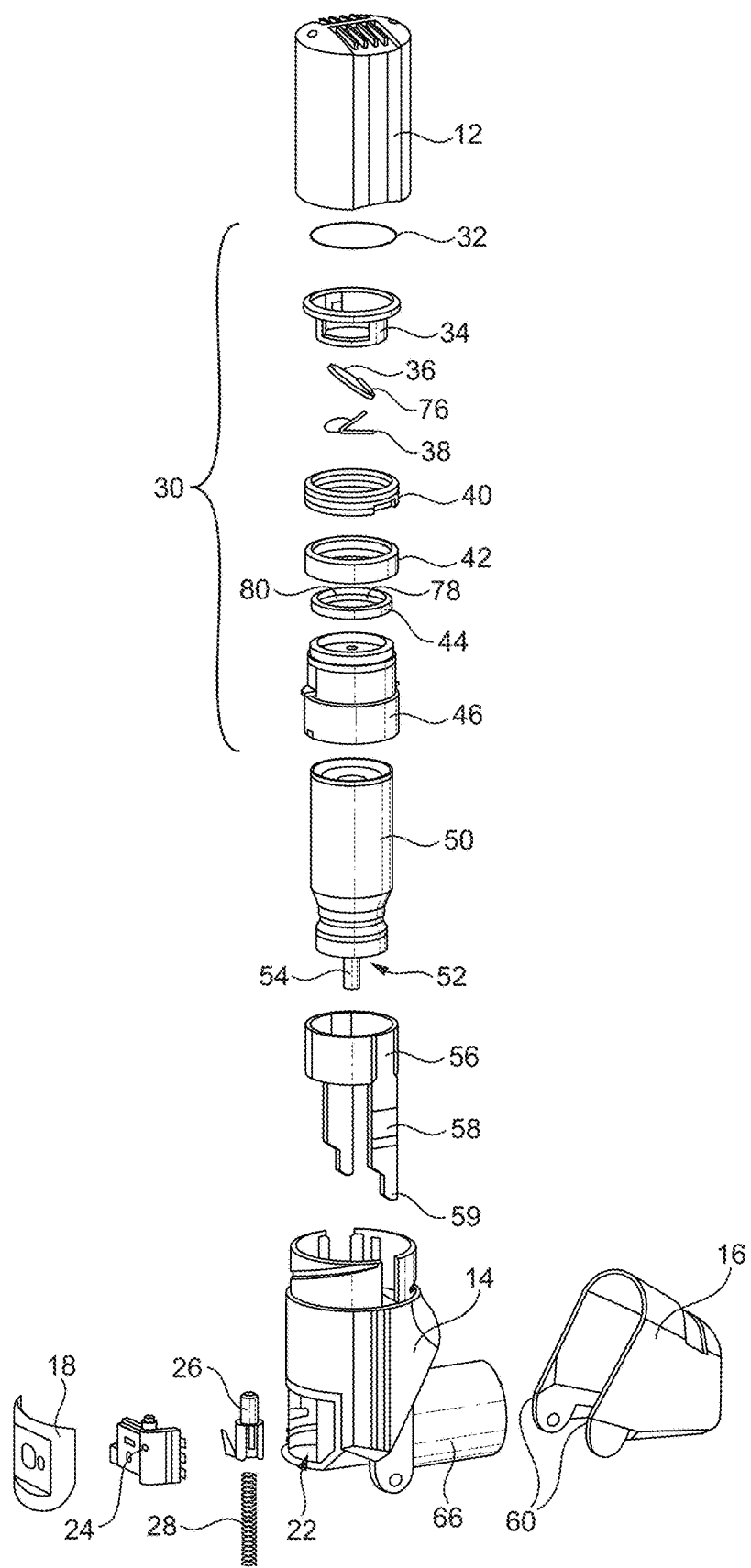
FIG. 8-9 shows a breath actuated metered dose inhaler according to the invention.

FIG. 8 shows a breath actuated inhaler which is merely an example of an inhaler in accordance with the present invention. The inhaler includes a force holding unit housing 12, a main body 14, a mouthpiece dust cap 16 and a dose counter door 18 having a dose counter window. In other embodiments comprising nasal inhalers, the mouthpiece 66 may be replaced with a nose piece.

As shown by the exploded view of FIG. 8, a dose counter chamber 22 includes a dose counter system 24 closed within it by the dose counter door 18. The dose counter system includes an actuating pin 26 and return spring 28. The dose counter can take various forms and may, for example, be as described in EP2135199A or EP2514464A.

As also shown in FIG. 8, the inhaler 10 includes a force holding unit 30 which includes: a filter 32, flap valve housing 34, flap valve 36, flap valve spring 38, compression spring 40, retaining ring 42, diaphragm 44 and lower cap 46. The inhaler also includes a canister 50 with a metering valve 52 and a valve stem 54; as well as a yoke 56 with drive rods or legs 58 having distal ends 59 which are driven by respective cams 60 on the pivotally-connected mouthpiece dust cap 16. The valve stem 54 may be fitted into an inner bore of a valve stem block which communicates with a nozzle (not shown) for ejection of inhalable substances through a central bore of a mouthpiece 66 (FIG. 8) of the main body 14 of the inhaler.

In embodiments, the arrangement of openings in the metering valve of the present invention is similar to those described in US2016/0084385, which is incorporated by reference herein. In particular, the metering valve of the present invention may be similar to the embodiment shown in FIG. 4 of US2016/0084385, in which the valve body includes at least one first opening (i.e., at least one first side hole 100 that is arranged in a cylindrical portion of the valve body) and at least one second opening (i.e., at least one second side hole 111 that, as with the first hole(s), is arranged in a cylindrical portion of the valve body), the second opening(s) being axially offset relative to the first opening(s) along a longitudinal axis that extends between a first axial end and a second axial end of the valve body. The first opening(s) and second opening(s) that are axially offset from each other along the valve body enable the metering chamber to be filled and emptied.

Figure 1:
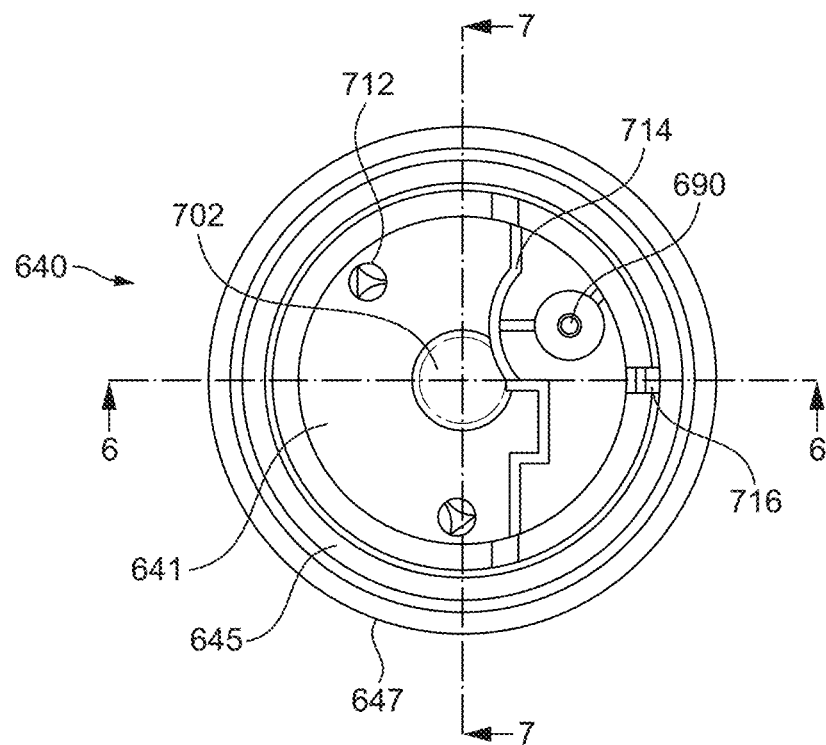
FIG. 1-3 show a known multi-material diaphragm for a breath actuated inhaler.
Figure 2:
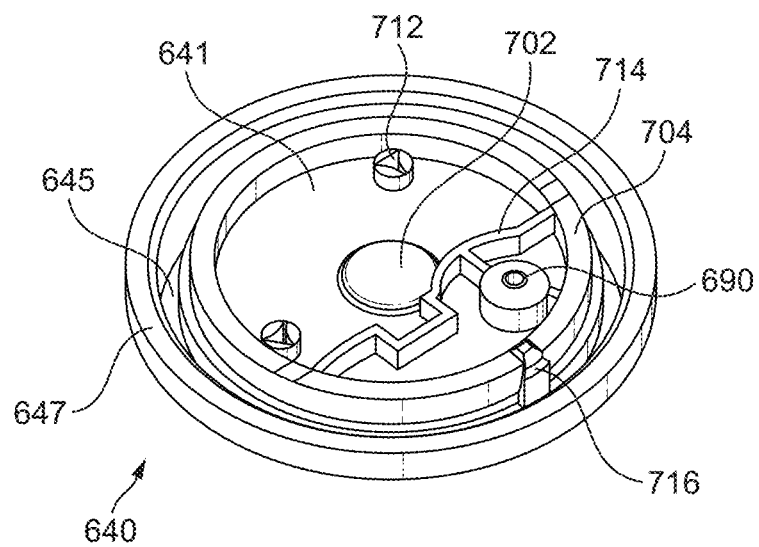
Figure 3:
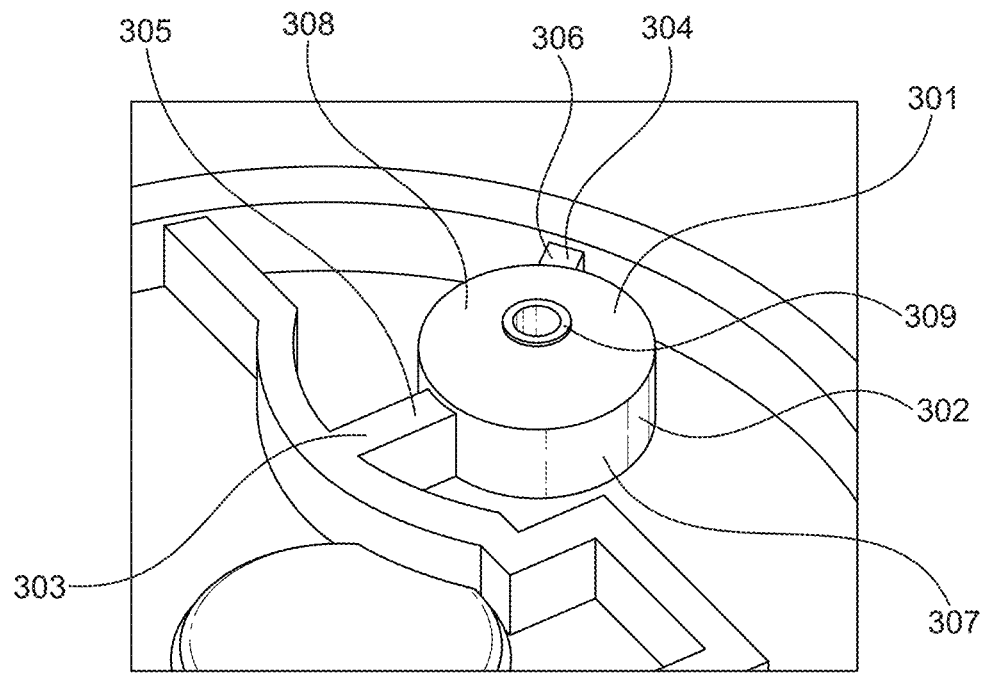

The force holding unit 30 operates substantially as disclosed with reference to FIGS. 1 to 3 of EP1289589A and the yoke 56 and mouthpiece dust cap 16 substantially as described in EP2514465A, including but not limited to FIG. 22 thereof, which are incorporated herein by reference.

Figure 9:
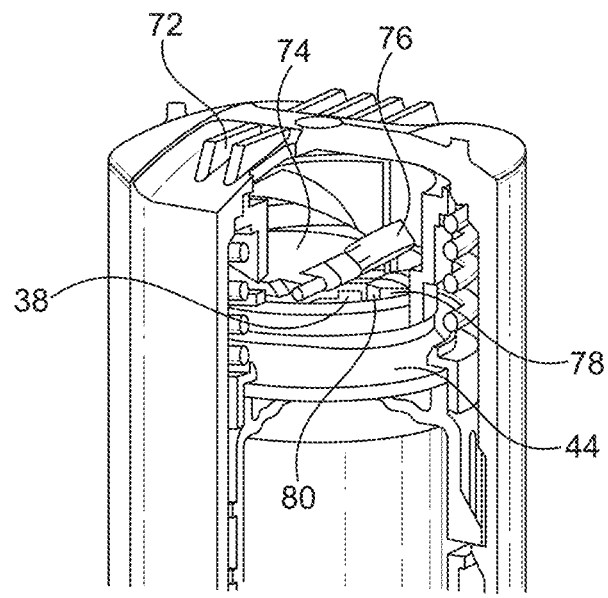

FIG. 9 shows the flap valve 36 and diaphragm 44 in situ, in a patient inhalation configuration, so at the spring 38, the upper surface of the boss 80, and the valve orifice channel 78 are visible.

The canister 50 is operable by a force holding unit 30 having a cap housing 12 attachable to a main body 14 of the inhaler. In use, a mouthpiece cap 16 is opened to prime the inhaler ready for inhalation and then after inhalation the mouthpiece cap 16 is closed to reset the force holding unit 30, i.e. return it to a rest configuration.

In more detail, when the mouthpiece cap 16 is opened, the lower cap 46 is forced downwards under the action of the compression spring 40. Then, as the lower cap 46 moves down, an enclosed volume between the diaphragm 44 and the lower cap 46 is increased by a linear amount, and whilst valve port remains closed, this creates a pressure difference in the enclosed volume.

The offset of the differential between the pressure in the enclosed volume and atmospheric pressure results in the lower cap 46 resisting action of the compression spring 40. Downward movement of the lower cap 46 continues until the force is balanced between the force of the compression spring 46 and the opposing forces of the pressure difference and metering valve 52.

The geometry of the mechanism is arranged such that the balance occurs before the valve has been actuated.

Upon inhalation, air enters the inhaler through approximately ten air inlets 72 formed on the cap housing 12. Flow of air across a vane 74 on the flap valve 36 during inhalation causes the valve 36 to pivot, moving the flap valve seal 76 out of its rest position, and opening a valve orifice channel 78 in the diaphragm 44. The subsequent passage of air into the volume between the diaphragm 44 and the lower cap 46 allows the volume to reach atmospheric pressure. The resulting imbalance of forces acting on the lower cap 46 and canister 50 produces the downward (forward) motion of the canister 50 and actuation of the aerosol metering valve 52: releasing a measured dose through the dispensing nozzle and into the mouthpiece 66.

The force holding unit 30 relies on the described pressure difference to maintain the prepared configuration, and release thereof for firing the canister 50 under the action of the compression spring 40. The force holding unit 30 is therefore considered pneumatic within the normal meaning of the term.

Figure 4:
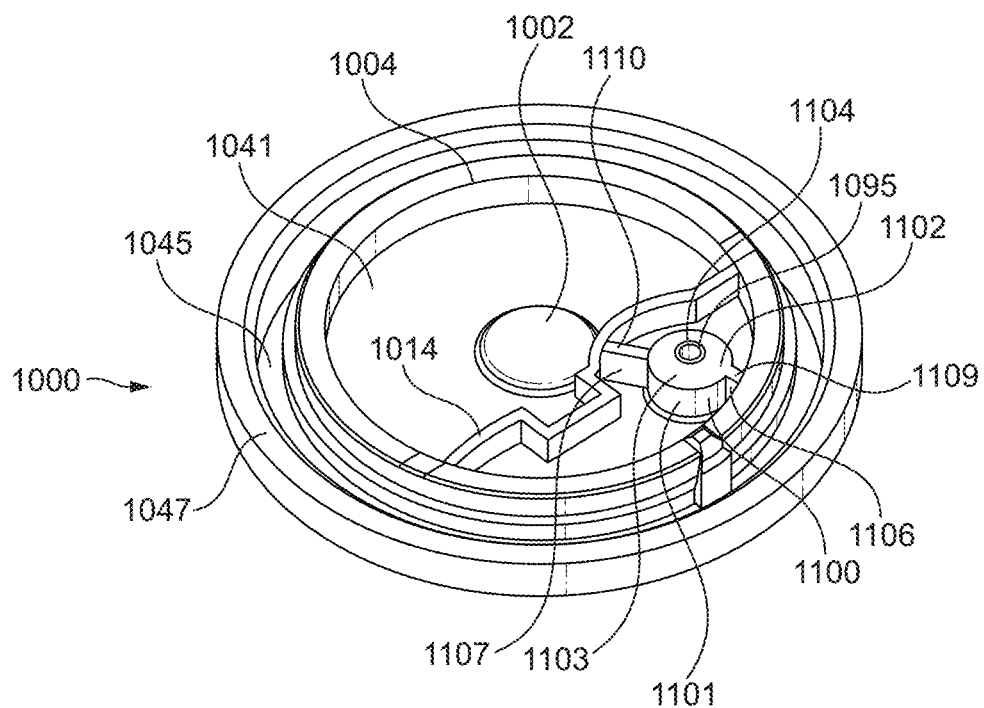
FIG. 4 shows a multi-material diaphragm according to the invention.

Referring to FIG. 4, a diaphragm 1000 according to the present invention for use with the medicament dispenser of FIGS. 8 and 9 is shown.

The moulded flexible diaphragm 1000 includes a rigid disc-like section 1041, a flexible generally cylindrical wall section, or annular flexure 1045, and a thicker connector section, or peripheral attachment ring 1047. A central portion (not shown) is unitarily formed with and extends radially inwardly from the annular flexure 1045. The central portion preferably is provided in the form of a disk bonded along a top surface to a bottom surface of the rigid disc-like section 1041.

The relatively thick disk-portion which includes the disc-like section 1041 of the diaphragm 1000, is moulded from acrylonitrile butadiene styrene, which is particularly resistant to flexural deformation. The relatively thin flexure portion which includes the central portion, the annular flexure 1045 and the peripheral attachment ring 1047, is moulded from thermoplastic polyurethane, permitting high performance flexibility. The multi-material diaphragm 1000 may be made using a multi-shot moulding process wherein the rigid disc-like section is moulded in a first step, and the second flexible portion is moulded in a second step, and at the same time bonded to the first portion.

As shown in FIG. 4, the rigid disc-like section 1041 defines a central upwardly extending boss 1002 for additional strength. In addition, the rigid disc-like section 1041 includes an outer axial wall 1004 which provides further strength to the diaphragm 1000.

The valve port 1095 of the diaphragm 1000 passes through the rigid disc-like section 1041 and the central portion of the diaphragm. The valve port 1095 is closed by the valve port seal 76, which is biased closed by a flat spring 38, as shown in FIG. 9. Although not shown, the rigid disc-like section 1041 of the diaphragm may include protrusions extending upwardly therefrom that receive the flat spring 38. The rigid disc-like section 1041 of the diaphragm 100 also includes a baffle 1014 on a top surface thereof for substantially preventing air flow between the valve port seal 76 and the diaphragm.

As illustrated in FIG. 4 the valve port 1095 comprises an annular boss 1100 projecting from an upper surface of the rigid disc-like portion 1041 of the diaphragm. Typically, the annular boss 1100 and rigid disk-like portion 1041 are a single unitary structure. The annular boss 1100 comprises a lower generally cylindrical body portion 1101 and an upper portion 1102 in the form of a truncated cone. The frustum of the truncated cone provides the upper surface 1103 of the annular boss 1100. The upper surface 1103 includes an annular projection 1104 which surrounds the entrance to the valve orifice channel and provides the sealing surface 1103, which in use engages the valve port seal in a sealing relation. Whilst the illustrated annular boss 1100, including both its upper 1102 and lower portions 1101, and the annular projection 1104, all have a circular circumference, it will be appreciated that other boss shapes may also be employed without departing from the invention. Accordingly, unless stated otherwise, for the purposes of the invention the use of annular, circumference, circumferential and/or radial, or the like, do not restrict the invention to circular cross-sectioned bodies. Equally, substantially circular cross-sectioned and/or circumferenced bodies are not excluded.

As illustrated, the valve port 1095 further comprises two radially outwardly extending projections 1106 and 1107. A first projection 1106 extending from outer wall 1004 to the annular boss 1100. The second projection extending from the baffle 1014 to the annular boss 1100. During moulding molten polymer, or prepolymer, flows along a path defined by the mould corresponding to each of the two projections 1106 1107 into the annular boss mould cavity. Typically, the projections are of substantially the same thickness 'T'. In this illustrated embodiment 0.64 mm. The illustrated projections 1106 1107 are substantially uniformly circumferentially separated. That is to say, each and every projection is separated from its adjacent projections by substantially the same central angle. The illustrated projections 1106 1107 are separated from each other by a central angle of 180 degrees. They are diametrically opposed. As illustrated by reference to FIG. 5 and FIG. 6, an imaginary straight-line Y running along a central axis of the projections passes through the central longitudinal axis X of the valve orifice channel. This arrangement concentrates polymer flow towards the centre of the boss 1100 during moulding, improving the surface finish of the upper surface 1103 and in particular its sealing surface 1105.

Figure 6:
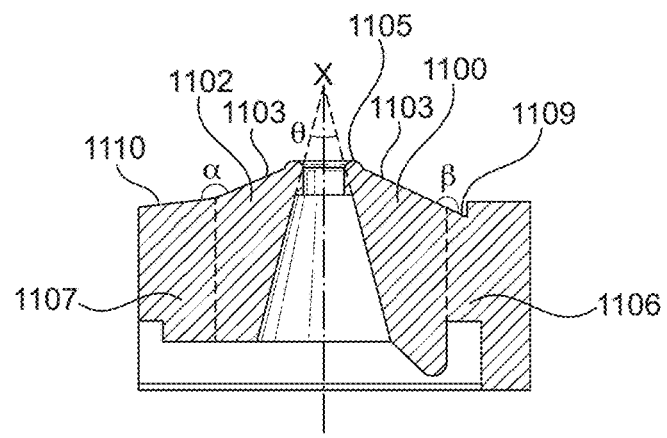

As better illustrated in FIG. 6, the upper surfaces of the first 1107 and the second projections 1106 are both contiguous with the upper surface 1103 of the annular boss 1100. The upper surface 1110 of the first projection 1107 and the upper surface 1103 of the annular boss 1100 are at an angle ($\alpha$) of greater than 90 degrees but less than 180 degrees. The upper surface 1109 of the second projection 1106 and the upper surface 1103 of the annular boss 1100 are at an angle ($\beta$) of approximately 180 degrees: preferably there is no discernible joint between the two.

As a result of each of the upper surfaces 1109 1110 of the projections 1106 1107 and the upper surface 1103 of the annular boss 1100 joining directly, during moulding, molten polymer is able to flow directly along the mould surface from projection upper surface to boss upper surface without stalling, improving the finish of the upper surface 1103 of the annular boss 1100 and in particular the sealing surface 1105.

As illustrated in FIG. 6 a portion of the valve orifice channel forms the frustum of an imaginary cone with an apex angle $\theta$ of 28 degrees. With reference to FIG. 14, the valve orifice channel 78 has a volume of 1.91 mm$^3$ and the annular boss 80 has a volume of 12.02 mm$^3$.

Figure 5:
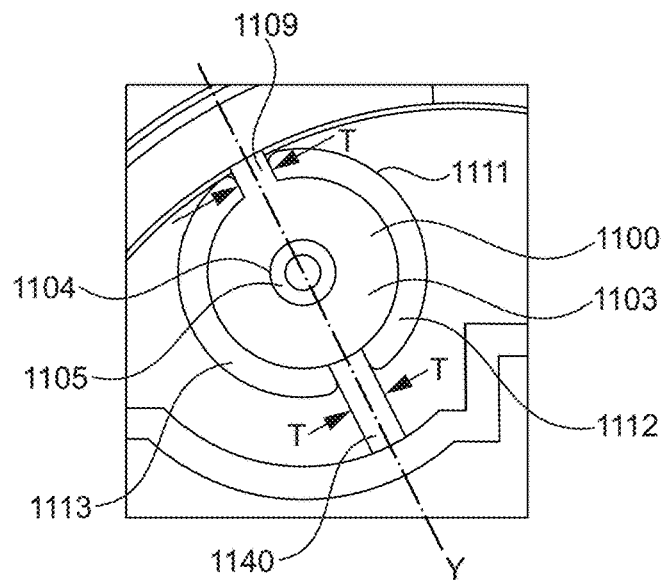
FIG. 5-7 show cross-sections of a valve port according to the invention.
Figure 7:
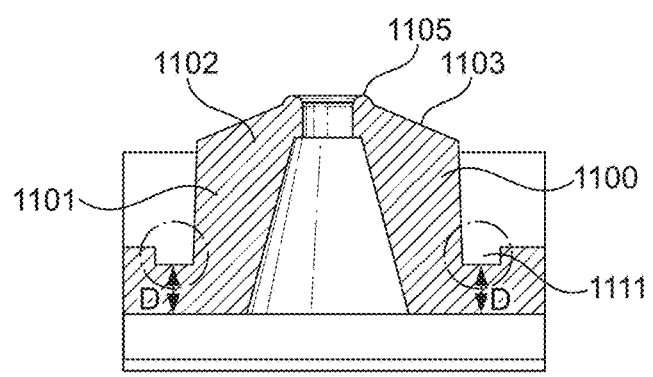

As better illustrated in FIGS. 5 and 7, the annular boss 1100 is surrounded by a circumferential channel 1111 formed in the upper surface of the diaphragm 1041 surrounding the annular boss 1100. The channel 1111 has two sections 1112 and 1113 each extending between the two projections 1106 and 1107 around opposite sides of the annular boss 1100. The channel sections 1112 and 1113 reduce the depth of the relatively rigid disk-like portion 1041 of the diaphragm immediately adjacent to the annular boss; typically, to a depth 'D' less than the thickness 'T' of the projections 1106 and 1107. This arrangement concentrates polymer flow towards the centre of the annular boss 1100 during moulding, improving the smoothness of the upper surface 1103 and in particular the sealing surface 1105.

Figure 10:
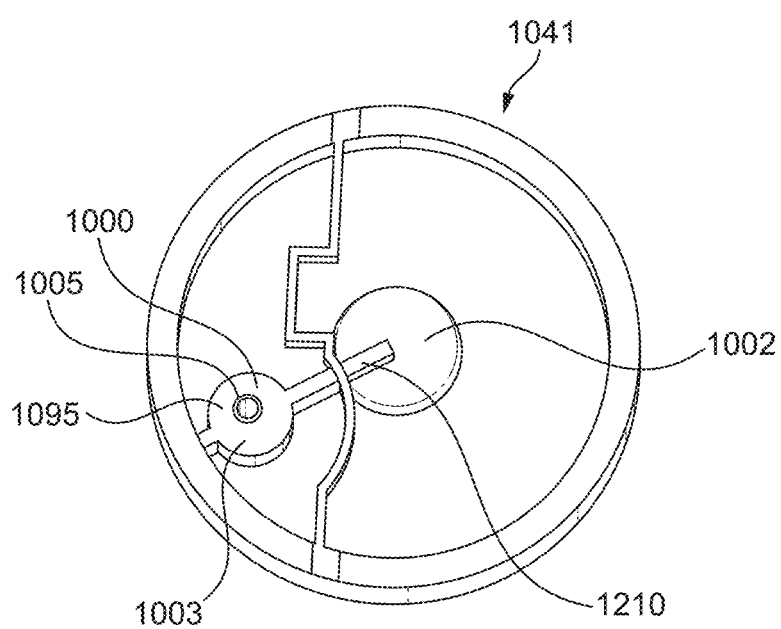
FIG. 10 shows an alternative diaphragm according to the invention.

FIG. 10 shows an alternative diaphragm central disk 1041 according to the invention. As illustrated, this embodiment differs from that illustrated in FIG. 4 in that one of the radially outwardly extending projections 1210 of the valve port 1095 extends from the annular boss 1100 to the central upwardly extending boss 1002. As with the valve port 1095 shown in FIG. 4, this arrangement concentrates polymer flow towards the centre of the annular boss 1100 during moulding, improving the smoothness of the upper surface 1003 and, in particular, the sealing surface 1005.

Advantageously, it has been found that injection moulded diaphragms according to the invention provide an increased yield during manufacturing compared to those illustrated in FIGS. 1-3 and improved surface finish immediately adjacent the valve channel orifice. In embodiments, the yield has increased from about 50% to about 85%.

In embodiments the breath actuated metered dose inhaler comprises a reservoir, particularly a pressurized canister, comprising an active pharmaceutical ingredient (API).

Preferably the active pharmaceutical ingredient is presented in a pharmaceutical composition comprising a propellant, optionally a co-solvent and optionally other pharmaceutically acceptable excipients.

Preferred propellants include hydrofluroalkanes, in particular 1,1,1,2-tetrafluoroethane (HFA134a), 1,1,1,2,3,3,3-heptafluoropropane (HFA227), or combinations thereof. Most particular propellant is HFA134a. Most particular HFA134a concentration is from about 91.8% w/w to 92.9% w/w.

HFA134a has a low boiling point (−261° C.) and correspondingly high vapor pressure (572 kpa) at 20° C.

Particular co-solvents are selected from the list of aliphatic alcohols (particularly ethanol), glycerols and glycols. Most particular co-solvent is ethanol. Most particular ethanol concentration is about 8% w/w.

Ethanol is well known to be compatible with HFA-134a and increases the solubility of BDP. Ethanol (anhydrous) is used as a co-solvent to aid solubility of BDP in HFA134a. A concentration of around 8% w/w of ethanol is known to provide necessary stability, preventing precipitation and achieving correct aerosol performance.

Other pharmaceutically acceptable excipients include surfactants, particularly oleic acid.

Preferably, the active pharmaceutical ingredient is suspended in the propellant. Alternatively, the active pharmaceutical ingredient is dissolved in the propellant. The active pharmaceutical ingredient may also be partly suspended and partly dissolved in the propellant.

A particular active pharmaceutical ingredient is selected from the group consisting of anti-inflammatory agents, β2-adrenoreceptor agonists, anti-cholinergic agents, antihistamines, serotonin agonists, and combinations thereof.

Suitable anti-inflammatory agents include corticosteroids and NSAIDs.

Suitable corticosteroids which may be used include those oral and inhaled corticosteroids and their pro-drugs which have anti-inflammatory activity. Examples of suitable corticosteroids include methyl prednisolone, dexamethasone, fluticasone propionate, fluticasone furoate, beclomethasone, beclomethasone esters such as e.g. the 17-propionate ester or the 17,21-dipropionate ester, budesonide, flunisolide, mometasone, mometasone esters such as e.g. the furoate ester, triamcinolone acetonide, rofleponide, ciclesonide, and butixocort propionate.

A particular corticosteroid is beclomethasone dipropionate (BDP).

Suitable NSAIDs include sodium cromoglycate, nedocromil sodium, phosphodiesterase (PDE) inhibitors (e, g, theophylline, PDE4 inhibitors or mixed PDE3/PDE4 inhibitors), leukotriene antagonists, inhibitors of leukotriene synthesis, iNOS inhibitors, tryptase and elastase inhibitors, beta-2-integrin antagonists and adenosine receptor agonists or antagonists (e. g. adenosine 2a agonists), cytokine antagonists (e.g. chemokine antagonists) or inhibitors of cytokine synthesis.

Suitable β2-adrenoreceptor agonists are selected from SABA (short-acting β2-adrenoreceptor agonists), LABA (long-acting β2-adrenoreceptor agonists), ultra-LABA (ultra-long-acting β2-adrenoreceptor agonists), and combinations thereof.

Suitable SABA include bitolterol, fenoterol, isoprenaline, orciprenaline, pirbuterol, procaterol, salbutamol, levosalbutamol, terbutaline, and pharmaceutically acceptable salts and esters thereof.

Suitable LABA include bambuterol, clenbuterol, formoterol, arformoterol, protokylol, salmeterol, and pharmaceutically acceptable salts and esters thereof.

Suitable ultra-LABA include indacaterol, olodaterol, vilanterol, and pharmaceutically acceptable salts and esters thereof.

Particularly suitable β2-adrenoreceptor agonists include salmeterol xinafoate, salbutamol sulphate, salbutamol free base, formoterol fumarate, fenoterol or terbutaline.

A particular β2-adrenoreceptor agonist is salbutamol sulphate.

Suitable anticholinergic agents are those compounds that act as antagonists at the muscarinic receptor, in particular those compounds, which are antagonists of the M1 and M2 receptors. Compounds include the alkaloid of the belladonna plants as illustrated by the likes of atropine, scopolamine, homatropine, hyoscyamine; these compounds are normally administered as a salt, being tertiary amines.

Particularly suitable anticholinergics include ipratropium (e.g. as the bromide), oxitropium (e. g. as the bromide) and tiotropium (e, g. as the bromide). Further suitable anticholinergics of interest are methantheline, propantheline bromide, anisotropine methyl bromide, clidinium bromide, copyrrolate, isopropamide iodide, mepenzolate bromide, tridihexethyl chloride, hexocyclium, cyclopentolate hydrochloride, tropicamide, trihexyphenidyl hydrochloride, pirenzepine, telenzepine, and methoctramine.

Suitable antihistamines (also referred to as H1-receptor antagonists) include carbinoxamine maleat, clemastine fumarate, diphenylhydramine hydrochloride, dimenhydrinate, pyrilamine maleate, tripelennamine HCl, tripelennamine citrate, chlorpheniramine, chlorpheniramine maleate, acrivastine, hydroxyzine HCl, hydroxyzine pamoate, cyclizine HCl, cyclizine lactate, meclizine HCl, cetirizine HCl, astemizole, levocabastine HCl, loratadine, loratadine descarboethoxy analogue, terfenadine, fexofenadine hydrochloride, azelastine hydrochloride.

In a particular embodiment of the invention, the active pharmaceutical ingredient is selected from beclomethasone dipropionate (BDP), salbutamol sulphate and dihydroergotamine.

In a particular embodiment the breath actuated metered dose inhaler comprises a pressurized canister comprising beclomethasone dipropionate as active pharmaceutical ingredient; HFA134a as propellant and ethanol as co-solvent.

In a particular embodiment the breath actuated metered dose inhaler comprises a pressurized canister comprising beclomethasone dipropionate as active pharmaceutical ingredient at about 1.0 mg/ml, HFA134a as propellant at about 1090.20 mg/ml and ethanol as co-solvent at about 94.80 mg/mi.

In a particular embodiment the breath actuated metered dose inhaler comprises a pressurized canister comprising beclomethasone dipropionate as active pharmaceutical ingredient at about 0.084% w/w, HFA134a as propellant at about 91.9% w/w and ethanol as co-solvent at about 8.0% w/w.

In a particular embodiment the breath actuated metered dose inhaler comprises a pressurized canister comprising beclomethasone dipropionate as active pharmaceutical ingredient at about 0.169% w/w, HFA134a as propellant at about 91.8% w/w and ethanol as co-solvent at about 8.0% w/w.

In a particular embodiment the breath actuated metered dose inhaler comprises a pressurized canister comprising salbutamol sulphate as active pharmaceutical ingredient, HFA134a as propellant and ethanol as co-solvent.

In a particular embodiment the breath actuated metered dose inhaler comprises a pressurized canister comprising about 0.1098 mg of salbutamol sulphate as active pharmaceutical ingredient, about 27.8 mg of HFA134a as propellant and about 3.6 mg of ethanol as co-solvent.

One embodiment relates to a breath actuated metered dose inhaler as described herein comprising an active pharmaceutical ingredient.

One embodiment relates to a breath actuated metered dose inhaler as described herein comprising an active pharmaceutical ingredient for therapeutic use.

One embodiment relates to a breath actuated metered dose inhaler as described herein comprising an active pharmaceutical ingredient for use in the treatment or prevention of a respiratory disease, particularly COPD or Asthma.

One embodiment relates to an active pharmaceutical ingredient for use in the treatment or prevention of a respiratory disease, particularly COPD or Asthma, wherein the active pharmaceutical ingredient is delivered to a patient using a breath actuated metered dose inhaler as described herein.

One embodiment relates to a method for the treatment or prevention of respiratory diseases, particularly COPD or Asthma, which method comprises administering an active pharmaceutical ingredient to a human being or animal using a breath actuated metered dose inhaler as described herein.

One embodiment relates to the use of a breath actuated metered dose inhaler as described herein comprising an active pharmaceutical ingredient for the treatment or prevention of respiratory diseases, particularly COPD or Asthma.

The invention will now be illustrated by the way of the following examples which are intended to be non-limiting.

Examples

Sample Preparation

Two groups of Easi-Breathe™ inhaler force holding unit diaphragms were prepared for use in the following examples.

The diaphragms in both groups shared the following common features.

The diaphragms of both groups were injection moulded on a Nestal 120 2-shot apparatus with 8+8 cavity mould and 25 mm/25 mm screw and barrel. In both groups the rigid disk-like portion was made from ABS Sabic Cycolac™ HMG47MD, and the central portion, the annular flexure and the peripheral attachment ring were moulded from an elastomer comprising 96% BASF Elastollan® 1185A with 4% BASF Konz 950/1 additive as release agent.

The first "control" group diaphragms (M30579) were manufactured according to FIGS. 1 to 3, with the injection moulding parameters as set out in Table 1.

Whereas, the second "test" group diaphragms (M24406) were manufactured according to FIG. 4, with the injection moulding parameters as set out in Table 2.

TABLE 1

| Parameter | Process Value | Minimum Value | Maximum Value |
| --- | --- | --- | --- |
| Diaphram-M24406 | | | |
| Injection Time | .13 sec. | .12 sec. | .14 sec. |
| Hold Pressure | 750 bar | 675 bar | 825 bar |
| Pack and Hold Time | 1.0 sec | .9 sec | 1.1 sec |
| Cool Time | 6.0 sec | 5.4 sec | 6.6 sec |
| Barrel Temp. | 210° C. | 205° C. | 215° C. |
| Mold Water (Front/Cavities) | 75° F. | 65° F. | 85° F. |
| Mold Water (Back/Cores) | 75° F. | 65° F. | 85° F. |
| 2nd Shot | | | |
| Injection Speed | 10 mm/s | 9 mm/s | 11 mm/s |
| Pack and Hold Pressure | 700 bar | 630 bar | 770 bar |
| Total Pack and Hold Time | 1.0 sec. | 1.0 sec. | 1.0 sec |
| Cool Time | 6.0 sec. | 6.0 sec. | 6.0 sec. |
| Barrel Temp. | 245° C. | 240° C. | 250° C. |

TABLE 2

| Parameter | Process Value | Minimum Value | Maximum Value |
| --- | --- | --- | --- |
| Diaphram-M30579 | | | |
| Injection Time | 1.26 sec. | 1.13 sec. | 1.39 sec. |
| Hold Pressure | 10153 psi | 8122 psi | 12183 psi |
| | 700 bar | 560 bar | 840 bar |
| Pack and Hold Time | 1.0 sec | 1.0 sec | 1.0 sec |
| Cool Time | 6.0 sec | 6.0 sec | 6.0 sec |
| Melt Temp. | 473° F. | 463° F. | 483° F. |
| | 245° C. | 240° C. | 250° C. |
| Mold Water (Front/Cavities) | 110° F. | 100° F. | 120° F. |
| | 43° C. | 38° C. | 48° C. |
| Mold Water (Back/Cores) | 110° F. | 100° F. | 120° F. |
| | 43° C. | 38° C. | 48° C. |
| 2nd Shot | | | |
| Injection Time | 0.12 sec. | 0.108 sec. | 0.132 sec. |
| Pack and Hold Pressure | 10153 psi | 8122 psi | 12183 psi |
| | 700 bar | 560 bar | 840 bar |
| Total Pack and Hold Time | 1.0 sec. | 1.0 sec. | 1.0 sec |
| Cool Time | 6.0 sec. | 6.0 sec. | 6.0 sec. |
| Melt Temp. | 410° F. | 400° F. | 420° F. |
| | 210° C. | 205° C. | 215° C. |

Surface Roughness

The surface roughness of the sealing surface of each diaphragm was analysed using Bruker Contour GT white light interferometry machine at a magnification of 27.5×. Three areas of were scanned on each sealing surface, i.e. those indicated by the three-pronged arrow in FIG. 13. Each scanning area was 230 μm×172 μm. The areas were selected so as to avoid any weld line.

The results are summarised in Table 3. The results show that the test diaphragms are less rough than control diaphragms.

Weld Line Measurements

Figure 11:
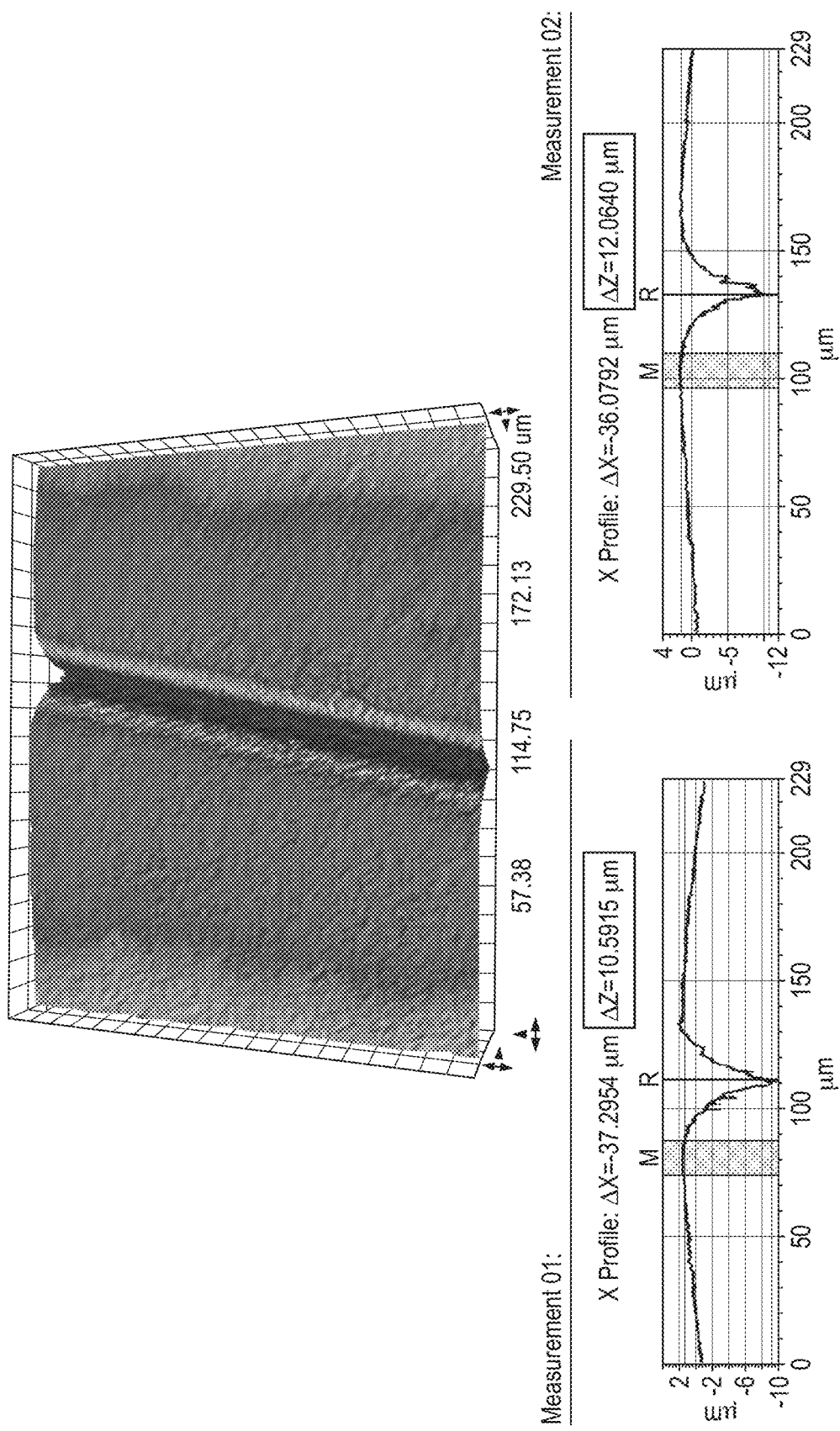
FIG. 11 shows surface roughness testing results of a known valve port sealing surface.
Figure 12:
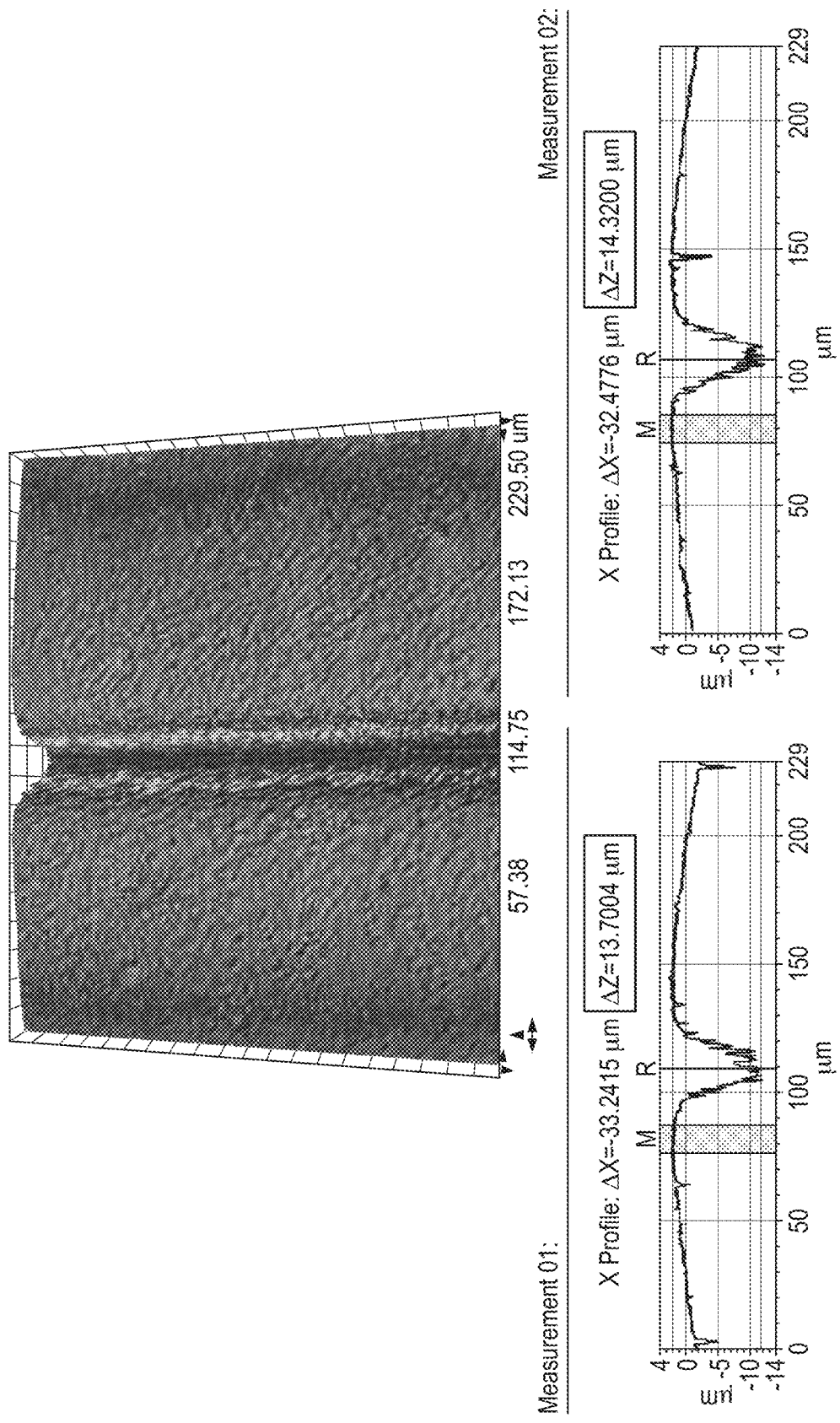
FIG. 12 shows surface roughness testing results of a valve port sealing surface according to the invention.
Figure 13:
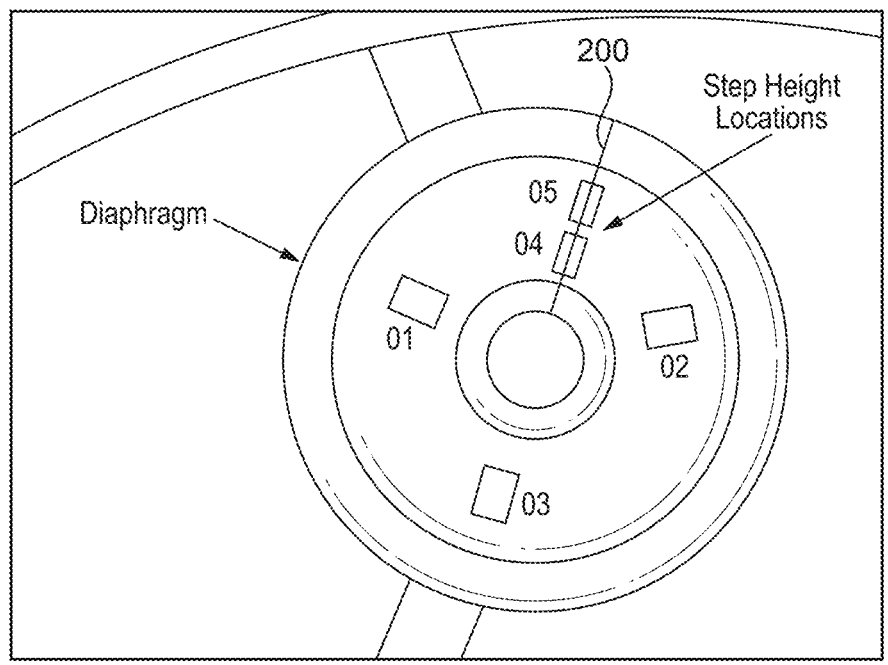
FIG. 13 shows the locations at which surface roughness measurements may be taken.

Using the Bruker Contour GT, the step height measurement mode was used to measure the depth of the weld line of the diaphragm samples and the step width measurement mode and Cross Sectioning was used to measure the width of the weld line. The location of the measurements are indicated in FIG. 13 by rectangles 4 and 5: labelled 'Step Height Locations". The weld line (200) is indicated. Example results are illustrated in FIGS. 11 and 12, and summarised in Table 3.

TABLE 3

|  | Control Diaphragm Design (n = 2) | Test Diaphragm Design (n = 2) |
| --- | --- | --- |
| Mean Roughness Average (RA)/μm | 0.162 | 0.095 |
| Mean Weld Line Depth/ μm | 11 | 13.95 |

Force Holding Unit Performance

Otherwise identical EasiBreathe™ force holding units (FHUs) were assembled comprising either the control or test diaphragms mentioned above. The ability of both types of FHU to retain a pressure difference after priming was then assessed using an Instron 5564 force testing unit according to the following method. The Instron was equipped with an Instron ±1 kN load cell and operated using Bluehill 2.33.895 software.

The FHU to be tested was secured in the Instron, with the Instron gripping the unit housing and the lower cap. The Instron was then used to compress the FHU until a force of 90N was achieved. Then the Instron was backed off 2.6 mm and a first, F1, force reading was recorded. The Instron was held in the same position for a period of 5 minutes, after which time a second force reading, F2, was taken.

The results are summarised in Tables 4 and 5.

TABLE 4

| Control Diaphragm Design (n = 10) | | | |
| --- | --- | --- | --- |
|  | F1 (N) | F2 (N) | Delta F1 − F2 (N) |
| Mean | 23.14 | 27.39 | 4.25 |
| Minimum | 22.72 | 24.34 | 1.48 |
| Maximum | 23.63 | 34.35 | 11.52 |

TABLE 5

| Test Diaphragm Design (n = 10) | | | |
| --- | --- | --- | --- |
|  | F1 (N) | F2 (N) | Delta F1 − F2 (N) |
| Mean | 21.701 | 22.034 | 0.333 |
| Minimum | 20.74 | 21.33 | 0.18 |
| Maximum | 22.2 | 22.42 | 0.59 |

As demonstrated, FHUs containing the test diaphragms according to the invention were able to maintain a pressure difference more effectively over the allotted time period.

The invention claimed is:

1. A breath actuated metered dose inhaler comprising:
a canister fire system configured to provide a canister actuation force to fire a medicament containing canister in response to patient inhalation, the canister fire system comprising a pneumatic force holding unit and having:
a rest configuration in which a metering valve of the canister is in a refill configuration;
a prepared configuration in which a canister actuation force is retained by a difference in pressure between an enclosed volume within the pneumatic force holding unit and atmospheric pressure, and in which prepared configuration the canister fire system is actuatable by patient inhalation induced airflow;
and a fire configuration in which the metering valve is in a dose delivery position;
wherein, in the prepared configuration, the force retained by the pneumatic force holding unit reduces but by less than about 6% over a period of 5 minutes.

2. The breath actuated metered dose inhaler of claim 1, wherein, when in the prepared configuration, the force retained by the pneumatic force holding unit reduces by less than about 3% over a period of 5 minutes.

3. The breath actuated metered dose inhaler of claim 1, further comprising at least one of:
a valve port for the pneumatic force holding unit, the valve port comprising an annular boss defining a valve orifice channel and two or more radially outwardly extending projections defining a path through which polymer passes to form the annular boss during injection molding, wherein the two or more radially outwardly extending projections are substantially uniformly circumferentially separated and the annular boss has a longitudinal axis which passes through the valve orifice channel, and wherein the at least two radially outwardly extending projections and the valve orifice channel lie in a common plane coincident with the longitudinal axis;
a flap valve comprising a chassis for pivotal mounting within the inhaler, a valve port seal mounted on the chassis configured to selectively engage the valve port in a sealing relation, and a vane for moving the valve port seal away from the valve port in response to inhalation induced airflow; and
a diaphragm comprising a rigid disk portion and a flexible membrane,
wherein the valve port is unitarily formed with the rigid disk portion.

4. The breath actuated metered dose inhaler according to claim 1 comprising a medicament for use in the treatment of a respiratory disease.

5. The breath actuated inhaler according to claim 4 wherein the respiratory disease is selected from COPD and asthma.

6. The breath actuated inhaler according to claim 5 wherein the medicament is selected from the group consisting of an anticholinergic and a corticosteroid.

7. The breath actuated inhaler according to claim 6, wherein the anticholinergic comprises tiotropium.

8. The breath actuated inhaler according to claim 6, wherein the corticosteroid comprises beclomethasone dipropionate.

9. The breath actuated inhaler of claim 1 wherein the pneumatic force holding unit comprises a valve port comprising a valve seal surface configured to be sealably engaged by a movable valve seal, wherein the valve seal surface has a surface roughness average (RA) of less than about 0.15 um.

10. A breath actuated metered dose inhaler comprising:
a canister fire system configured to provide a canister actuation force to fire a medicament containing canister in response to patient inhalation, the canister fire system comprising a pneumatic force holding unit and having:
a rest configuration in which a metering valve of the canister is in a refill configuration;
a prepared configuration in which a canister actuation force is retained by a difference in pressure between an enclosed volume within the pneumatic force holding unit and atmospheric pressure, and in which prepared configuration the canister fire system is actuatable by patient inhalation induced airflow;

and a fire configuration in which the metering valve is in a dose delivery position;

wherein, in the prepared configuration, the force retained by the pneumatic force holding unit reduces but by less than about 6% over a period of 5 minutes and wherein the pneumatic force holding unit further comprises a valve port comprising a relatively rigid valve seal surface configured to be sealably engaged by an elastomeric valve seal, wherein the relatively rigid valve seal surface has a surface roughness average (RA) of less than about 0.15 μm.

* * * * *